US009968679B2

(12) United States Patent
Shikamura et al.

(10) Patent No.: US 9,968,679 B2

(45) Date of Patent: May 15, 2018

(54) CLEAR AQUEOUS SOLUTION

(71) Applicant: SENJU PHARMACEUTICAL CO., LTD., Osaka-shi, Osaka (JP)

(72) Inventors: Yuko Shikamura, Hyogo (JP); Yuka Higashimura, Hyogo (JP)

(73) Assignee: SENJU PHARMACEUTICAL CO., LTD., Osaka (JP)

(*) Notice: Subject to any disclaimer, the term of this patent is extended or adjusted under 35 U.S.C. 154(b) by 0 days. days.

(21) Appl. No.: 14/763,304

(22) PCT Filed: Jan. 30, 2014

(86) PCT No.: PCT/JP2014/052041

§ 371 (c)(1),
(2) Date: Jul. 24, 2015

(87) PCT Pub. No.: WO2014/119643

PCT Pub. Date: Aug. 7, 2014

(65) Prior Publication Data

US 2015/0366969 A1 Dec. 24, 2015

(30) Foreign Application Priority Data

Jan. 31, 2013 (JP) ................................ 2013-017876
Dec. 25, 2013 (JP) ................................ 2013-267724

(51) Int. Cl.

| | |
|---|---|
| *A61K 31/427* | (2006.01) |
| *A61K 47/18* | (2017.01) |
| *A61K 9/08* | (2006.01) |
| *A61K 9/00* | (2006.01) |
| *A61K 47/10* | (2017.01) |

(52) U.S. Cl.

CPC .......... *A61K 47/186* (2013.01); *A61K 9/0048* (2013.01); *A61K 9/08* (2013.01); *A61K 31/427* (2013.01); *A61K 47/10* (2013.01)

(58) Field of Classification Search

CPC .................................................. A61K 31/427

See application file for complete search history.

(56) References Cited

U.S. PATENT DOCUMENTS

| | | | |
|---|---|---|---|
| 7,119,104 | B2 | 10/2006 | Sakuma et al. |
| 7,402,597 | B2 | 7/2008 | Sakuma et al. |
| 7,888,370 | B2 | 2/2011 | Singh et al. |
| 8,129,431 | B2 | 3/2012 | Sawa et al. |
| 8,143,312 | B2 | 3/2012 | Asada et al. |
| 8,173,671 | B2 | 5/2012 | Singh et al. |
| 8,183,291 | B2 | 5/2012 | Asada et al. |
| 8,497,304 | B2 | 7/2013 | Sawa et al. |
| 8,669,290 | B2 | 3/2014 | Sawa et al. |
| 8,754,131 | B2 | 6/2014 | Sawa et al. |
| 8,802,705 | B2 | 8/2014 | Nakamura et al. |
| 8,871,813 | B2 | 10/2014 | Sawa et al. |
| 8,927,606 | B1 | 1/2015 | Sawa et al. |
| 9,144,609 | B2 | 9/2015 | Sawa et al. |
| 2005/0096363 | A1 | 5/2005 | Sakuma et al. |
| 2005/0239895 | A1 | 10/2005 | Sawa et al. |
| 2006/0069162 | A1 | 3/2006 | Asada et al. |
| 2007/0027196 | A1 | 2/2007 | Sakuma et al. |
| 2009/0137539 | A1 | 5/2009 | Singh et al. |
| 2010/0190833 | A1 | 7/2010 | Nakamura et al. |
| 2010/0331407 | A1 | 12/2010 | Asada et al. |
| 2011/0082125 | A1 | 4/2011 | Singh et al. |
| 2012/0115957 | A1 | 5/2012 | Sawa et al. |
| 2012/0184552 | A1 | 7/2012 | Nakajima et al. |
| 2012/0270910 | A2 | 10/2012 | Nakamura et al. |
| 2013/0090384 | A1 | 1/2013 | Sawa et al. |
| 2014/0142183 | A1 | 5/2014 | Sawa et al. |
| 2014/0235721 | A1 | 8/2014 | Sawa et al. |
| 2014/0243413 | A1 | 8/2014 | Sawa et al. |
| 2014/0343109 | A1 | 11/2014 | Nakamura et al. |
| 2015/0011634 | A1 | 1/2015 | Sawa et al. |
| 2015/0025149 | A1 | 1/2015 | Sawa et al. |
| 2015/0366966 | A1 | 12/2015 | Shikamura et al. |

FOREIGN PATENT DOCUMENTS

| | | | |
|---|---|---|---|
| CN | 1700913 | | 11/2005 |
| EP | 2952109 | | 12/2015 |
| JP | H02-83318 | A | 3/1990 |
| JP | H11-228404 | A | 8/1999 |
| JP | 2003-160491 | A | 6/2003 |
| JP | 2004-123729 | A | 4/2004 |
| RU | 2010126096 | | 11/2009 |
| WO | WO 2003/033493 | A1 | 4/2003 |
| WO | WO 2008/143254 | A1 | 11/2008 |
| WO | WO 2011/034192 | A1 | 3/2011 |

OTHER PUBLICATIONS

Search Report issued by the Patent Office of the Russian Federation, dated Jan. 11, 2018, dated Feb. 1, 2018 (3 pages).

Office Action issued for the corresponding Russian Patent Application No. 2015135974, dated Jan. 11, 2018, dated Feb. 1, 2018 (11 pages).

General Pharmacopoeial Article, "Defining transparency and the degree of turbidity of liquids," Ministry of Health of the Republic of Belarus (Jan. 2, 2011) (5 pages).

M. C. Prieto-Blanco et al., "Analysis of Residual Products in Benzalkonium Chloride by High-Performance Liquid Chromatography," Journal of Chromatographic Science, vol. 37, Aug. 1999, pp. 295-299.

(Continued)

*Primary Examiner* — Zohreh A Fay

(74) *Attorney, Agent, or Firm* — Finnegan, Henderson, Farabow, Garrett & Dunner LLP

(57) ABSTRACT

The present invention provides a stable and clear aqueous liquid preparation containing (3-{2-[4-isopropyl-2-(4-trifluoromethyl)phenyl-5-thiazolyl]ethyl}-5-methyl-1,2-benzisoxazol-6-yl)oxyacetic acid or a pharmaceutically acceptable salt thereof as an active ingredient, and benzalkonium chloride represented by the formula:

$$[C_6H_5CH_2N(CH_3)_2R]Cl$$

wherein R is an alkyl group having 8-18 carbon atoms.

28 Claims, No Drawings

(56) References Cited

Y. Xue et al., “Kinetic characteristics and toxic effects of benzalkonium hloride following intravascular and oral administration in rats,” Journal of Chromatography B, vol. 811, 2004, pp. 53-58.
J. Mehta et al., “Development and Validation of a Precise Method for Determination of Benzalkonium Chloride (BKC) Preservative, in Pharmaceutical Formulationof Latanoprost Eye Drops,” E-Journal of Chemistry, vol. 7(1), 2010, pp. 11-20.
U.S Pharmacopeia online entry for Benzalkonium Chloride, vol. No. 27(4), p. 2789, accessed Mar. 6, 2018 (2 pages), http://www.pharmacopeia.cn/v29240/usp29nl24s0_m7800.html.

CLEAR AQUEOUS SOLUTION

TECHNICAL FIELD

The present invention relates to a method of clearing an aqueous liquid preparation containing (3-{2-[4-isopropyl-2-(4-trifluoromethyl)phenyl-5-thiazolyl]ethyl}-5-methyl-1,2-benzisoxazol-6-yl)oxyacetic acid or a pharmaceutically acceptable salt thereof, and a clear aqueous liquid preparation containing (3-{2-[4-isopropyl-2-(4-trifluoromethyl)phenyl-5-thiazolyl]ethyl}-5-methyl-1,2-benzisoxazol-6-yl)oxyacetic acid or a pharmaceutically acceptable salt thereof, which is superior in preservation stability.

BACKGROUND ART

It has been reported that (3-{2-[4-isopropyl-2-(4-trifluoromethyl)phenyl-5-thiazolyl]ethyl}-5-methyl-1,2-benzisoxazol-6-yl)oxyacetic acid or a pharmaceutically acceptable salt thereof (hereinafter sometimes to be abbreviated as "compound A") is a medicament having a Peroxisome Proliferator-Activated Receptor (hereinafter to be abbreviated as PPAR) δ agonist action (see patent document 1). In addition, patent document 2 describes that compound A is a PPAR δ agonist and useful as a proliferation promoter of meibomian gland epithelial cell or corneal epithelial cell.

DOCUMENT LIST

Patent Documents patent document 1: WO 03/033493
patent document 2: WO 2008/143254

SUMMARY OF THE INVENTION

Problems to be Solved by the Invention

As a preservative for aqueous liquid preparations such as ophthalmic solutions and the like, benzalkonium chloride (hereinafter to be abbreviated as BAK) is used most generally. BAK, cationic species, is known to cause an interaction such as salt formation and the like with a compound having an anionic group such as carboxy group and the like, which may produce white turbidity in aqueous liquid preparations.

Means of Solving the Problems

The present inventors have conducted intensive studies in an attempt to solve the above-mentioned problems and found that a colorless, clear aqueous liquid preparation free of white turbidity and superior in preservation stability can be provided by adding a particular concentration of BAK having an alkyl group with a particular chain length solely or as a mixture of plural BAKs having alkyl group with different chain lengths to an aqueous liquid preparation containing compound A as an active ingredient, which resulted in the completion of the present invention.

Accordingly, the present invention relates to

[1] an aqueous liquid preparation comprising (3-{2-[4-isopropyl-2-(4-trifluoromethyl)phenyl-5-thiazolyl]ethyl}-5-methyl-1,2-benzisoxazol-6-yl)oxyacetic acid or a pharmaceutically acceptable salt thereof, and benzalkonium chloride represented by the formula:

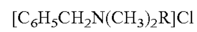

$[C_6H_5CH_2N(CH_3)_2R]Cl$ wherein R is an alkyl group having 8-18 carbon atoms, which has transmittance at wavelength 600 nm of not less than 98%,

[2] the aqueous liquid preparation of the above-mentioned [1], wherein (3-{2-[4-isopropyl-2-(4-trifluoroxmethyl)phenyl-5-thiazolyl]ethyl}-5-methyl-1,2-benzisoxazol-6-yl)oxyacetic acid or a pharmaceutically acceptable salt thereof has a concentration selected from the range of the lower limit concentration of about 0.0002 w/v % and the upper limit concentration of about 0.05 w/v % relative to the total amount of the aqueous liquid preparation,

[3] the aqueous liquid preparation of the above-mentioned [1] or [2], wherein R is an alkyl group having 8 carbon atoms, and benzalkonium chloride contained therein has a concentration of less than 0.05 w/v % or higher than 0.1 w/v % relative to the total amount of the aqueous liquid preparation,

[4] the aqueous liquid preparation of the above-mentioned [1] or [2], wherein R is an alkyl group having 10 carbon atoms, and benzalkonium chloride contained therein has a concentration of less than 0.05 w/v % or higher than 0.1 w/v % relative to the total amount of the aqueous liquid preparation,

[5] the aqueous liquid preparation of the above-mentioned [1] or [2], wherein R is an alkyl group having 12 carbon atoms, and benzalkonium chloride contained therein has a concentration of less than 0.003 w/v % or higher than 0.01 w/v % relative to the total amount of the aqueous liquid preparation,

[6] the aqueous liquid preparation of the above-mentioned [1] or [2], wherein R is an alkyl group having 14 carbon atoms, and benzalkonium chloride contained therein has a concentration of less than 0.001 w/v % or higher than 0.002 w/v % relative to the total amount of the aqueous liquid preparation,

[7] the aqueous liquid preparation of the above-mentioned [1] or [2], wherein R is an alkyl group having 16 carbon atoms, and benzalkonium chloride contained therein has a concentration other than 0.001 w/v % relative to the total amount of the aqueous liquid preparation,

[8] the aqueous liquid preparation of the above-mentioned [1] or [2], wherein R of benzalkonium chloride is an alkyl group having 18 carbon atoms,

[9] the aqueous liquid preparation of the above-mentioned [1] or [2], wherein benzalkonium chloride comprises benzalkonium chloride wherein R is an alkyl group having 12 carbon atoms and benzalkonium chloride wherein R is an alkyl group having 14 carbon atoms, and a total concentration of benzalkonium chloride relative to the total amount of the aqueous liquid preparation is less than 0.001 w/v % or higher than 0.002 w/v %,

[10] The aqueous liquid preparation of any of the above-mentioned [1]-[9], further comprising a surfactant,

[11] the aqueous liquid preparation of the above-mentioned [10], wherein the surfactant is tyloxapol,

[12] the aqueous liquid preparation of any of the above-mentioned [1]-[11], which is for ophthalmology,

[13] the aqueous liquid preparation of the above-mentioned [12], which is an ophthalmic solution,

[14] an ophthalmic solution comprising (3-{2-[4-isopropyl-2-(4-trifluoromethyl)phenyl-5-thiazolyl]ethyl}-5-methyl-1,2-benzisoxazol-6-yl)oxyacetic acid or a pharmaceutically acceptable salt thereof, benzalkonium chloride represented by the formula:

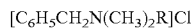

$[C_6H_5CH_2N(CH_3)_2R]Cl$ wherein R is an alkyl group having 8-18 carbon atoms, and tyloxapol, which has transmittance at wavelength 600 nm of not less than 98%,

[15] a method of clearing an aqueous liquid preparation comprising (3-{2-[4-isopropyl-2-(4-trifluoromethyl)phenyl-5-thiazolyl]ethyl}-5-methyl-1,2-benzisoxazol-6-yl) oxyacetic acid or a pharmaceutically acceptable salt thereof, comprising adding benzalkonium chloride represented by the formula:

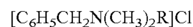

$[C_6H_5CH_2N(CH_3)_2R]Cl$ wherein R is an alkyl group having 8-18 carbon atoms,

[16] the method of the above-mentioned [15], wherein benzalkonium chloride wherein R is an alkyl group having 8 carbon atoms is added at a concentration of less than 0.05 w/v % or higher than 0.1 w/v % relative to the total amount of the aqueous liquid preparation,

[17] the method of the above-mentioned [15], wherein benzalkonium chloride wherein R is an alkyl group having 10 carbon atoms is added at a concentration of less than 0.05 w/v % or higher than 0.1 w/v % relative to the total amount of the aqueous liquid preparation,

[18] the method of the above-mentioned [15], wherein benzalkonium chloride wherein R is an alkyl group having 12 carbon atoms is added at a concentration of less than 0.003 w/v % or higher than 0.01 w/v % relative to the total amount of the aqueous liquid preparation,

[19] the method of the above-mentioned [15], wherein benzalkonium chloride wherein R is an alkyl group having 14 carbon atoms is added at a concentration of less than 0.001 w/v % or higher than 0.002 w/v % relative to the total amount of the aqueous liquid preparation,

[20] the method of the above-mentioned [15], wherein benzalkonium chloride wherein R is an alkyl group having 16 carbon atoms is added at a concentration other than 0.001 w/v % relative to the total amount of the aqueous liquid preparation,

[21] the method of the above-mentioned [15], wherein benzalkonium chloride wherein R is an alkyl group having 18 carbon atoms is added, and

[22] the method of the above-mentioned [15], wherein a mixture concurrently containing benzalkonium chloride wherein R is an alkyl group having 12 carbon atoms and benzalkonium chloride wherein R is an alkyl group having 14 carbon atoms at a concentration of less than 0.001 w/v % or higher than 0.002 w/v % relative to the total amount of the aqueous liquid preparation.

Effect of the Invention

According to the present invention, a colorless clear aqueous liquid preparation containing compound A useful as a therapeutic agent for diseases such as meibomian gland dysfunction, corneal epithelial disorder, dry eye and the like, and a production method thereof can be provided.

DESCRIPTION OF EMBODIMENTS

The present invention is further explained in detail in the following.

In the present specification, unless particularly indicated, w/v % means weight per volume percentage in the Japanese Pharmacopoeia, 16th Edition. Unless particularly indicated, the contact lens encompasses any type of contact lens such as hard, oxygen permeable hard, soft and the like.

In the present specification, an aqueous solution being "clear" means, unless particularly indicated, a state of light transmittance at wavelength 600 nm of not less than 98%, wherein a colorless one is indicated as "colorless clear". In addition, a state of light transmittance of an aqueous solution of less than 98.0% is indicated as a state of being cloudy, i.e., white turbid state.

In the present invention, BAK means a compound having a chemical structure represented by the formula:

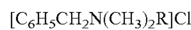

$[C_6H_5CH_2N(CH_3)_2R]Cl$ wherein P is an alkyl group having 8-18 carbon atoms. The compound encompasses not only a single compound wherein R is solely an alkyl group having the same chain length but also a mixture of plural compounds wherein R is an alkyl group having a different chain length.

The Japanese, US and European Pharmacopoeias define as follows.

The Japanese Pharmacopoeia, 16th Edition, defines that BAK is shown by $[C_6H_5CH_2N(CH_3)_2R]Cl$ wherein R is $C_8H_{17}$—$C_{18}H_{37}$, and mainly composed of $C_{12}H_{25}$ and $C_{14}H_{29}$.

The US Pharmacopoeia defines that the BAK is a mixture of alkylbenzyldimethyl ammonium chloride shown by $[C_6H_5CH_2N(CH_3)_2R]Cl$, wherein R is a mixture of all or some alkyl groups each having a chain longer than $C_8H_{17}$, and mostly constituted of $C_{12}H_{25}$, $C_{14}H_{29}$ and $C_{16}H_{33}$.

The European Pharmacopoeia defines that it is a mixture of alkylbenzyldimethylammonium chloride, wherein alkyl group has a chain length of from C8 to C18.

A mixture of plural BAKs wherein R has an alkyl, group having a different chain length is available as, for example, Sanisol C (manufactured by Kao Corporation), Osvan S (manufactured by Nihon Pharmaceutical Co., Ltd.), Benzalkonium Chloride Solution 50% Ph. Eur., USP/NF (manufactured by FeF Chemicals A/S) and the like.

A compound wherein R is an alkyl group of any of $C_8H_{17}$—$C_{18}H_{37}$ (specifically, for example, $C_{10}H_{21}$, $C_{12}H_{25}$, $C_{14}H_{29}$, $C_{16}H_{33}$, $C_{18}H_{37}$ etc.) is commercially available as a single compound. For example, it is available as Benzyldimethyldecylammonium chloride ($R=C_{10}H_{21}$) (SIGMA-ALDRICH), Benzyldimethyldodecylammonium chloride ($R=C_{12}H_{25}$) (Fluka), Benzyldimethyltetradecylammonium chloride ($R=C_{14}H_{29}$) (Fluka), Benzyldimethylhexadecylammonium chloride, hydrate ($R=C_{16}H_{33}$) (Acros Organics), Benzyldimethylstearylammonium chloride, hydrate ($R=C_{18}H_{37}$) (manufactured by Tokyo Chemical Industry Co., Ltd.) and the like.

The aqueous liquid preparation in the present invention can be used for the treatment of diseases such as meibomian gland dysfunction, corneal epithelial disorder, dry eye and the like due to the PPAR $\delta$ agonist action of compound A.

Compound A used in the present invention includes any pharmaceutically acceptable salt. Examples of the pharmaceutically acceptable salt include, but are not limited to, salts with inorganic base such as sodium, potassium, calcium, magnesium, aluminum and the like, ammonium salt, salts with organic base such as methylamine, triethylamine, diethylamine, morpholine, piperazine, pyrrolidine, picoline, ethanolamine, lysine, arginine and the like. Compound A can be produced according to, for example, the method described in WO 03/033493 or a method analogous thereto.

In the aqueous liquid preparation of the present invention, the ratio of compound A to be added is not particularly limited as long as the effect of the present invention can be afforded. For example, the lower limit is generally about 0.00001 w/v %, preferably about 0.0001 w/v %, particularly preferably about 0.0002 w/v %, most preferably about 0.0005 w/v %, and the upper limit is generally about 1 w/v %, preferably about 0.1 w/v %, particularly preferably about 0.05 w/v %, most preferably about 0.005 w/v %, relative to the total amount of the aqueous liquid preparation.

The clear aqueous liquid preparation of the present invention can be prepared by adding and dissolving compound A in an aqueous solution of a particular concentration of BAK.

The content ratio of BAK to be used for the aqueous liquid preparation of the present invention may be appropriately determined according to the administration form and the amount of compound A to be added. The upper limit is about 5 w/v % and the lower limit is about 0.0001 w/v %, relative to the total amount of the aqueous liquid preparation. When used as an aqueous ophthalmic liquid preparation, the upper limit is about 0.02 w/v % and the lower limit is about 0.0001 w/v %, relative to the total amount of the aqueous liquid preparation. Use of BAK at a concentration higher than the upper limit is not preferable since eye irritancy becomes strong and corneal disorder may be induced. At a concentration lower than the lower limit, BAK does not function sufficiently as a preservative.

The amount of BAK necessary for preparing the clear aqueous liquid preparation of the present invention is defined as follows according to the carbon number of alkyl group R of BAK.

In an aqueous liquid preparation containing BAK wherein R is an alkyl group having 8 carbon atoms ($C_8H_{17}$) (hereinafter to be abbreviated as BAK-$C_8$), the concentration of BAK-$C_8$ is less than 0.05 w/v % (preferably not more than 0.03 w/v %, more preferably not more than 0.01 w/v %), or higher than 0.1 w/v % (preferably, not less than 0.2 w/v %, more preferably not less than 0.5 w/v %) relative to the total amount of the aqueous liquid preparation. When used as an ophthalmic aqueous liquid preparation, the concentration of BAK-$C_8$ is not more than 0.02 w/v % (preferably within the range of not less than 0.0005 w/v % and not more than 0.01 w/v %) relative to the total amount of the aqueous liquid preparation.

In an aqueous liquid preparation containing BAK wherein R is an alkyl group having 10 carbon atoms ($C_{10}H_{21}$) (hereinafter to be abbreviated as BAK-$C_{10}$), the concentration of BAK-$C_{10}$ is less than 0.05 w/v % (preferably not more than 0.03 w/v %, more preferably not more than 0.01 w/v %), or higher than 0.1 w/v % (preferably, not less than 0.2 w/v %, more preferably not less than 0.5 w/v %) relative to the total amount of the aqueous liquid preparation. When used as an ophthalmic aqueous liquid preparation, the concentration of BAK-$C_{10}$ is not more than 0.02 w/v % (preferably within the range of not less than 0.0005 w/v % and not more than 0.01 w/v %) relative to the total amount of the aqueous liquid preparation.

In an aqueous liquid preparation containing BAK wherein R is an alkyl group having 12 carbon atoms ($C_{12}H_{25}$) (hereinafter to be abbreviated as BAK-$C_{12}$), the concentration of BAK-$C_{12}$ is less than 0.003 w/v % (preferably not more than 0.002 w/v %), or higher than 0.01 w/v % (preferably, not less than 0.02 w/v %) relative to the total amount of the aqueous liquid preparation. When used as an ophthalmic aqueous liquid preparation, the concentration of BAK-$C_{12}$ is less than 0.003 w/v % (preferably within the range of not less than 0.0005 w/v % and not more than 0.002 w/v %), or higher than 0.01 w/v % (preferably within the range of higher than 0.01 w/v % and not more than 0.02 w/v %), relative to the total amount of the aqueous liquid preparation.

In an aqueous liquid preparation containing BAK wherein R is an alkyl group having 14 carbon atoms ($C_{14}H_{29}$) (hereinafter to be abbreviated as BAK-$C_{14}$), the concentration of BAK-$C_{14}$ is less than 0.001 w/v % or higher than 0.002 w/v % (preferably not less than 0.003 w/v %, more preferably not less than 0.005 w/v %) relative to the total amount of the aqueous liquid preparation. When used as an ophthalmic aqueous liquid preparation, the concentration of BAK-$C_{14}$ is less than 0.001 w/v % (preferably within the range of not less than 0.0005 w/v % and less than 0.001 w/v %), or higher than 0.002 w/v % (preferably within the range of not less than 0.005 w/v % and not more than 0.02 w/v %), relative to the total amount of the aqueous liquid preparation.

In an aqueous liquid preparation containing BAK wherein R is an alkyl group having 16 carbon atoms ($C_{16}H_{33}$) (hereinafter to be abbreviated as BAK-$C_{16}$), the concentration of BAK-$C_{16}$ is selected from a range other than 0.001 w/v % (preferably less than 0.001 w/v % or not less than 0.002 w/v %) relative to the total amount of the aqueous liquid preparation. When used as an ophthalmic aqueous liquid preparation, the concentration of BAK-$C_{16}$ is preferably within the range of not less than 0.0005 w/v % and less than 0.001 w/v % or not less than 0.002 w/v % and not more than 0.02 w/v %, relative to the total amount of the aqueous liquid preparation.

In an aqueous liquid preparation containing BAK wherein R is an alkyl group having 18 carbon atoms ($C_{18}H_{37}$) (hereinafter to be abbreviated as BAK-$C_{18}$), a colorless clear aqueous liquid preparation can be obtained regardless of the concentration of BAK-$C_{18}$ to be added. When used as an ophthalmic aqueous liquid preparation, the concentration of BAK-$C_{18}$ can be freely determined within a preferable range of not less than 0.0005 w/v % and not more than 0.02 w/v % relative to the total amount of the aqueous liquid preparation.

When a mixture of plural compounds wherein R has an alkyl group having different chain length is used as BAK, a concentration range that does not cause white turbidity can be determined by calculating a concentration of each BAK having alkyl group R with each carbon number at an addition concentration as a BAK mixture, and considering a concentration range affording a clear aqueous liquid preparation when each BAK with each alkyl chain length is added singly.

When present as a mixture of plural compounds having alkyl group R having different chain length (BAK mixture), the mixing ratio of respective BAKs having alkyl group RP with each carbon number is not particularly limited. Preferred as BAK is a mixture of BAK-$C_{12}$ and BAK-$C_{14}$, or a mixture of BAK-$C_{12}$, BAK-$C_{14}$ and BAK-$C_{16}$.

The appropriate pH range in the aqueous liquid preparation of the present invention varies depending on the application site, dosage form and the like, and is generally about 6.0-8.6. The pH can be adjusted by using buffering agent, pH adjuster and the like described below and according to a method known in the technical field.

Various additives such as buffering agent, isotonicity agent, solubilizing agent, surfactant, stabilizer, chelating agent, cooling agent, thickener, pH adjuster and the like can be added as necessary to the aqueous liquid preparation of the present invention.

Examples of the buffering agent include known boric acid buffers (borax etc.), citrate buffer (sodium citrate etc.), carbonate buffer (sodium hydrogen carbonate, sodium carbonate etc.), tartrate buffer (sodium tartrate etc.), gluconate buffer (sodium gluconate etc.), acetate buffer (sodium acetate etc.), phosphate buffer (sodium monohydrogen phosphate, sodium dihydrogen phosphate etc.), various amino acids such as glutamic acid, epsilon aminocaproic acid and the like, Tris buffer, Good buffer (MES, MOPS, PIPES, HEPES, BES, TES etc.) and the like, or a combination thereof.

Examples of the isotonicity agent include polyvalent alcohols such as sorbitol, glucose, mannitol, glycerin, propylene glycol and the like, salts such as sodium chloride, potassium chloride and the like, boric acid and the like.

Examples of the solubilizing agents include polyvinylpyrrolidone, polyethylene glycol, propylene glycol, sodium carboxymethylcellulose, glycerin and the like.

While the surfactant is not particularly limited, for example, non-ionic surfactants such as tyloxapol, polyoxyethylene hydrogenated castor oil 60, polysorbate 80, polysorbate 20, polyoxyl 40 stearate, octoxynol and the like are preferable. Of these, tyloxapol is particularly preferable, since it can improve stability of compound A in an aqueous liquid preparation.

When tyloxapol is added as a surfactant to the aqueous liquid preparation of the present invention, the amount of tyloxapol to be added may be appropriately determined according to the amount of compound A to be added. The lower limit of tyloxapol is generally about 0.001 w/v %, preferably about 0.01 w/v %, more preferably about 0.05 w/v %, and the upper limit is generally about 1.0 w/v %, preferably about 0.5 w/v %, more preferably about 0.2 w/v %, particularly preferably about 0.1 w/v %, relative to the total amount of the aqueous liquid preparation. In addition, in the aqueous liquid preparation of the present invention, besides tyloxapol, other conventional surfactants usable for ophthalmic application can be used in an appropriate combination, as long as the stability of compound A is not impaired.

Examples of the stabilizer include sodium edetate, sodium thiosulfate, thioglycolic acid, sodium thioglycolate, cysteine hydrochloride, ascorbic acid, cyclodextrin, condensed phosphoric acid or a salt thereof, sulfite, citric acid or a salt thereof, dibutylhydroxytoluene and the like.

Examples of the chelating agent include sodium edetate, sodium citrate, thioglycolic acid, sodium thioglycolate, thiolactic acid, thioglycerin, condensed phosphoric acid or a salt thereof (condensed sodium phosphate etc.) and the like.

Examples of the thickener include methylcellulose, hydroxyethylcellulose, hydroxypropylcellulose, hydroxypropylmethylcellulose, sodium chondroitin sulfate, sodium carboxymethylcellulose, polyvinylpyrrolidone, polyvinyl alcohol, polyethylene glycol and the like.

Examples of the pH adjuster include sodium hydroxide, potassium hydroxide, sodium carbonate, sodium hydrogen carbonate, boric acid or a salt thereof (borax), hydrochloric acid, citric acid or a salt thereof (sodium citrate, sodium dihydrogen citrate etc.), phosphoric acid or a salt thereof (disodium hydrogen phosphate, potassium dihydrogen phosphate etc.), acetic acid or a salt thereof (sodium acetate, ammonium acetate etc.), tartaric acid or a salt thereof (sodium tartrate etc.), amines such as monoethanolamine, diethanolamine, triethanolamine, meglumine and the like, and the like.

Examples of the cooling agent include menthol, borneol, camphor, mentha oil, eucalyptus oil, peppermint oil and the like. These may be any of d form, l form and dl form.

The aqueous liquid preparation to be used in the present invention can be used, for example, as ophthalmic solution, eye wash, agent for contact lenses and the like, and an ophthalmic solution is preferable. Preferable examples of the administration method include, but are not particularly limited to, dropwise administration such as instillation and the like and the like.

The aforementioned agents for contact lenses can be applied to various contact lenses including hard contact lenses and soft contact lenses.

The form of the ophthalmic solution of the present invention is preferably an aqueous solution.

The ophthalmic solution of the present invention is produced according to a preparation method known per se (e.g., the method described in the Japanese Pharmacopoeia, 16th Edition, Preparation General Rules, section of ophthalmic liquids and solutions, and the like). For example, the ophthalmic solution of the present invention can be produced by dissolving BAK, and other additives such as buffering agent, isotonicity agent and the like in distilled water or purified water, then dissolving compound A, adjusting the osmotic pressure and pH to predetermined levels, and sterilizing the mixture by filtration and aseptically filling same in a washed and sterilized container under aseptic environment.

When formulated as an ophthalmic solution, the aqueous liquid preparation is preferably contained in an instillation container provided with a liquid injection pore having a small diameter that can control droplet amount to facilitate dropping to the eyes. While the material of the container is not particularly limited, a container having low moisture permeability, a container to which respective components do not easily adsorb, a container having high transparency and the like are preferable. Specifically, for example, as the material of the container, synthetic resin, glass, cellulose, pulp and the like are used. From the aspects of squeezability and durability, the container is preferably made of a synthetic resin. Specific examples of the synthetic resin include polyethylene resin (e.g., low density polyethylene or high density polyethylene), polypropylene resin, ethylene-propylene copolymer resin, poly(ethylene terephthalate) resin, polycarbonate resin and the like.

Examples of the instillation container include a container wherein a spigot member and a container body, which are independently molded, are fit into an integrally-molded container wherein a liquid is tightly sealed simultaneously with the molding of the container (e.g., WO 2004/006826) and the like. When an integrally-molded container is employed, the container is superior in the aspect of cost or hygiene, since the container and the aqueous liquid preparation are continuously produced. The instillation container may be a unit dose type container to be disposed after each time of use (e.g., JP-A-9-207959). In addition, these containers may be adhesion-packed with a OV blocking film. Furthermore, the containers may be colored to enhance the UV blockiig performance.

When the aqueous liquid preparation of the present invention is used as an ophthalmic solution, it is generally administered by adding dropwise 1-2 drops, i.e., about 20-200 μL per instillation, to one eye 1-8 times per day, though subject to variation depending on the administration form, age, body weight and conditions of the subject of administration, treatment object and the like. In addition, several mL of the eye wash of the present invention is used for washing one time, and washing is performed once to several times per day.

EXAMPLES

While the present invention is explained in detail by referring to the following Experimental Examples and Formulation Examples, they do not limit the present invention, and the present invention may be modified without departing from the scope of the invention. In the following Experimental Examples and Formulation Examples, (3-{2-[4-isopropyl-2-(4-trifluoromethyl)phenyl-5-thiazolyl]ethyl}-5-methyl-1,2-benzisoxazol-6-yl)oxyacetic acid was used as compound A.

Experimental Example 1

Observation of Appearance of Compound A-containing Aqueous Liquid Preparation Due to Addition of BAK (Experiment Method)

An aqueous liquid preparation of compound A was prepared according to the following formulation. In purified water was dissolved sodium dihydrogen phosphate dihydrate or boric acid, and the mixture was adjusted to pH 7.5 or 8.5 by adding sodium hydroxide. Compound A was added to this solution and completely dissolved therein. Where necessary, the mixture was heated (about 60° C.-80° C.) and sonicated (42 kHz, 1 min). Then, BAK was added, and purified water was added to a prescribed amount to give an aqueous liquid preparation. The aqueous liquid preparation was filled in a glass ampoule, and color tone (white background was used) and clarity (black or white background was used) were visually observed. In addition, by using self-recording spectrophotometer (U-3000, U-3010, Hitachi, Ltd.), the light transmittance of said aqueous liquid preparation at wavelength 600 nm was measured. As the criteria of turbidity, a state of transmittance of not less than 98.0% was evaluated as colorless clear and less than 98.0% as white turbidity from the results of the visual observation.

TABLE 1

| | Example 1 | Example 2 | Example 3 | Example 4 | Example 5 | Comparative Example 1 | Comparative Example 2 |
|---|---|---|---|---|---|---|---|
| Compound A | 0.001 | 0.001 | 0.001 | 0.001 | 0.001 | 0.001 | 0.001 |
| sodium dihydrogen phosphate | 0.1 | 0.1 | 0.1 | 0.1 | 0.1 | 0.1 | 0.1 |
| BAK-$C_{10}$ | 0.0005 | 0.005 | 0.01 | 0.5 | 5.0 | 0.05 | 0.1 |
| sodium hydroxide | q.s. | q.s. | q.s. | q.s. | q.s. | q.s. | q.s. |
| purified water | q.s | q.s | q.s | q.s | q.s | q.s | q.s |
| pH | 7.5 | 7.5 | 7.5 | 7.5 | 7.5 | 7.5 | 7.5 |
| appearance (visual observation) | colorless clear | colorless clear | colorless clear | colorless clear | colorless clear | white turbidity | white turbidity |
| transmittance (600 nm) | 99.8% | 99.5% | 99.2% | 99.8% | 99.5% | 84.6% | 77.2% |

(unit of numerical values in Table: w/v %; q.s.: appropriate amount)

TABLE 2

| | Example 6 | Example 7 | Example 8 | Example 9 | Example 10 | Comparative Example 3 | Comparative Example 4 | Comparative Example 5 |
|---|---|---|---|---|---|---|---|---|
| Compound A | 0.001 | 0.001 | 0.001 | 0.001 | 0.001 | 0.001 | 0.001 | 0.001 |
| sodium dihydrogen phosphate | 0.1 | 0.1 | 0.1 | 0.1 | 0.1 | 0.1 | 0.1 | 0.1 |
| BAK-$C_{12}$ | 0.0005 | 0.001 | 0.002 | 0.02 | 0.1 | 0.003 | 0.005 | 0.01 |
| sodium hydroxide | q.s. | q.s. | q.s. | q.s. | q.s. | q.s. | q.s. | q.s. |
| purified water | q.s. | q.s. | q.s. | q.s. | q.s. | q.s. | q.s. | q.s. |
| pH | 7.5 | 7.5 | 7.5 | 7.5 | 7.5 | 7.5 | 7.5 | 7.5 |
| appearance (visual observation) | colorless clear | colorless clear | colorless clear | colorless clear | colorless clear | white turbidity | white turbidity | white turbidity |
| transmittance (600 nm) | 99.4% | 99.2% | 98.0% | 98.0% | 98.7% | 97.3% | 82.7% | 86.2% |

(unit of numerical values in Table: w/v %; q.s.: appropriate amount)

TABLE 3

| | Example 11 | Example 12 | Example 13 | Example 14 | Example 15 | Example 16 | Comparative Example 6 | Comparative Example 7 |
|---|---|---|---|---|---|---|---|---|
| Compound A | 0.001 | 0.001 | 0.001 | 0.001 | 0.001 | 0.001 | 0.001 | 0.001 |
| BAK-$C_{12}$ | 0.0005 | 0.001 | 0.002 | 0.05 | 0.1 | 0.5 | 0.005 | 0.01 |
| boric acid | 0.1 | 0.1 | 0.1 | 0.1 | 0.1 | 0.1 | 0.1 | 0.1 |
| sodium hydroxide | q.s. | q.s. | q.s. | q.s. | q.s. | q.s. | q.s. | q.s. |

TABLE 3-continued

| | Example 11 | Example 12 | Example 13 | Example 14 | Example 15 | Example 16 | Comparative Example 6 | Comparative Example 7 |
|---|---|---|---|---|---|---|---|---|
| purified water | q.s. | q.s. | q.s. | q.s. | q.s. | q.s. | q.s. | q.s. |
| pH | 8.5 | 8.5 | 8.5 | 8.5 | 8.5 | 8.5 | 8.5 | 8.5 |
| appearance (visual observation) | colorless clear | colorless clear | colorless clear | colorless clear | colorless clear | colorless clear | white turbidity | white turbidity |
| transmittance (600 nm) | 99.5% | 99.5% | 98.4% | 99.6% | 99.6% | 99.8% | 79.8% | 87.5% |

(unit of numerical values in Table: w/v %; q.s.: appropriate amount)

TABLE 4

| | Example 17 | Example 18 | Example 19 | Example 20 | Comparative Example 8 | Comparative Example 9 |
|---|---|---|---|---|---|---|
| Compound A | 0.005 | 0.005 | 0.005 | 0.005 | 0.005 | 0.005 |
| BAK-$C_{12}$ | 0.0005 | 0.001 | 0.05 | 0.5 | 0.005 | 0.01 |
| boric acid | 0.1 | 0.1 | 0.1 | 0.1 | 0.1 | 0.1 |
| sodium hydroxide | q.s. | q.s. | q.s. | q.s. | q.s. | q.s. |
| purified water | q.s. | q.s. | q.s. | q.s. | q.s. | q.s. |
| pH | 8.5 | 8.5 | 8.5 | 8.5 | 8.5 | 8.5 |
| appearance (visual observation) | colorless clear | colorless clear | colorless clear | colorless clear | white turbidity | white turbidity |
| transmittance (600 nm) | 99.3% | 98.8% | 98.0% | 99.6% | 84.2% | 81.5% |

(unit of numerical values in Table: w/v %; q.s.: appropriate amount)

TABLE 5

| | Example 21 | Example 22 | Example 23 | Comparative Example 10 | Comparative Example 11 |
|---|---|---|---|---|---|
| Compound A | 0.001 | 0.001 | 0.001 | 0.001 | 0.001 |
| sodium dihydrogen phosphate | 0.1 | 0.1 | 0.1 | 0.1 | 0.1 |
| BAK-$C_{14}$ | 0.0005 | 0.005 | 0.01 | 0.001 | 0.002 |
| sodium hydroxide | q.s. | q.s. | q.s. | q.s. | q.s. |
| purified water | q.s. | q.s. | q.s. | q.s. | q.s. |
| pH | 7.5 | 7.5 | 7.5 | 7.5 | 7.5 |
| appearance (visual observation) | colorless clear | colorless clear | colorless clear | white turbidity | white turbidity |
| transmittance (600 nm) | 99.3% | 99.3% | 99.5% | 88.4% | 87.6% |

(unit of numerical values in Table: w/v %; q.s.: appropriate amount)

TABLE 6

| | Example 24 | Example 25 | Example 26 | Example 27 | Comparative Example 12 |
|---|---|---|---|---|---|
| Compound A | 0.001 | 0.001 | 0.001 | 0.001 | 0.001 |
| sodium dihydrogen phosphate | 0.1 | 0.1 | 0.1 | 0.1 | 0.1 |
| BAK-$C_{16}$ | 0.0005 | 0.002 | 0.005 | 0.01 | 0.001 |
| sodium hydroxide | q.s. | q.s. | q.s. | q.s. | q.s. |
| purified water | q.s. | q.s. | q.s. | q.s. | q.s. |
| pH | 7.5 | 7.5 | 7.5 | 7.5 | 7.5 |
| appearance (visual observation) | colorless clear | colorless clear | colorless clear | colorless clear | white turbidity |
| transmittance (600 nm) | 99.5% | 99.7% | 99.8% | 99.7% | 96.0% |

(unit of numerical values in Table: w/v %; q.s.: appropriate amount)

TABLE 7

| | Example 28 | Example 29 | Example 30 | Example 31 | Example 32 |
|---|---|---|---|---|---|
| Compound A | 0.001 | 0.001 | 0.001 | 0.001 | 0.001 |
| sodium dihydrogen phosphate | 0.1 | 0.1 | 0.1 | 0.1 | 0.1 |
| BAK-$C_{18}$ | 0.0005 | 0.001 | 0.002 | 0.005 | 0.01 |
| sodium hydroxide | q.s. | q.s. | q.s. | q.s. | q.s. |
| purified water | q.s. | q.s. | q.s. | q.s. | q.s. |

TABLE 7-continued

| | Example 28 | Example 29 | Example 30 | Example 31 | Example 32 |
|---|---|---|---|---|---|
| pH | 7.5 | 7.5 | 7.5 | 7.5 | 7.5 |
| appearance (visual observation) | colorless clear | colorless clear | colorless clear | colorless clear | colorless clear |
| transmittance (600 nm) | 99.6% | 99.0% | 99.7% | 99.8% | 99.8% |

(unit of numerical values in Table: w/v %; q.s.: appropriate amount)

(Experiment Results)

As shown in Tables 1-7, it was found that a concentration range free of occurrence of white turbidity varies depending on the kind of BAK to be added. That is, when BAK-$C_{10}$ was used as BAK, a colorless clear aqueous liquid preparation was obtained by adding BAK-$C_{10}$ at a concentration of not more than 0.01 w/v % or not less than 0.5 w/v % (Table 1). When BAK-$C_{12}$ was used, a colorless clear aqueous liquid preparation was obtained by adding BAK-$C_{12}$ at a concentration of not more than 0.002 w/v % or not less than 0.02 w/v % (Table 2-Table 4). When BAK-$C_{14}$ was used, a colorless clear aqueous liquid preparation was obtained by adding BAK-$C_{14}$ at a concentration of not less than 0.0005 w/v % and less than 0.001 w/v % or not less than 0.005 w/v % (Table 5). When BAK-$C_{16}$ was used, a colorless clear aqueous liquid preparation was obtained by adding BAK-$C_{16}$ at a concentration of 0.0005 w/v % or not less than 0.002 w/v % (Table 6). When BAK-$C_{18}$ was used, a colorless clear aqueous liquid preparation was obtained by adding BAK-$C_{18}$ at any concentration (Table 7). According to the results of Table 2-Table 4, it was found that when the pH of the aqueous liquid preparation was within the range of 7.5-8.5, a colorless clear aqueous liquid preparation was obtained by the addition of a similar concentration of BAK-$C_{12}$, regardless of the changes in pH or concentration of compound A to be added.

Experimental Example 2

Observation of Appearance of Compound A-containing Aqueous Liquid Preparation by the Addition of 4:6 Mixture of BAK-$C_{12}$ and BAK-$C_{14}$ (Hereinafter to be Abbreviated as BAK-$C_{12}$/$C_{14}$)

(Experiment Method)

The following compound A-containing aqueous liquid preparations were prepared in the same manner as in Experimental Example 1, the color and clarity thereof were visually observed, and the transmittance of said aqueous liquid preparations at wavelength 600 nm was measured and evaluated.

TABLE 8

| | Example 33 | Example 34 | Example 35 | Comparative Example 13 | Comparative Example 14 |
|---|---|---|---|---|---|
| Compound A | 0.001 | 0.001 | 0.001 | 0.001 | 0.001 |
| sodium dihydrogen phosphate | 0.1 | 0.1 | 0.1 | 0.1 | 0.1 |
| BAK-$C_{12}$/$C_{14}$ | 0.0005 | 0.005 | 0.01 | 0.001 | 0.002 |
| sodium hydroxide | q.s. | q.s. | q.s. | q.s. | q.s. |
| purified water | q.s. | q.s. | q.s. | q.s. | q.s. |
| pH | 7.5 | 7.5 | 7.5 | 7.5 | 7.5 |
| appearance (visual observation) | colorless clear | colorless clear | colorless clear | nearly clear | white turbidity |
| transmittance (600 nm) | 99.6% | 99.5% | 99.8% | 97.9% | 80.7% |

(unit of numerical values in Table: w/v %; q.s.: appropriate amount)

(Experiment Results)

According to the results of Table 8, it was found that aqueous liquid preparations similar in appearance to those obtained by the addition of the aforementioned BAK-$C_{12}$ or BAK-$C_{14}$ alone were obtained even when BAK-$C_{12}$/$C_{14}$ was used.

Experimental Example 3

Observation of Appearance of Compound A-containing Aqueous Liquid Preparation by the Addition of Commercially Available BAK Mixture (Experiment Method)

In the same manner as in Experimental Example 1 except that tyloxapol was added and dissolved in purified water, the following compound A-containing aqueous liquid preparations were prepared, the color and clarity thereof were visually observed, and the transmittance of said aqueous liquid preparations at wavelength 600 nm was measured and evaluated.

The mixing ratio of each BAK in the below-mentioned commercially available BAK mixtures was quantified by high performance liquid chromatography (HPLC). The results are shown in Table 10.

Sanisol C (manufactured by Kao Corporation, production No.: 4888)

Osvan S (manufactured by Nihon Pharmaceutical Co., Ltd., production No.: S277)

Benzalkonium Chloride Solution 50% Ph. Eur., USP/NF (manufactured by FeF Chemicals A/S, Batch No.: 209634)

HPLC Analysis Conditions measuring device: HPLC system (manufactured by Shimadzu Corporation, LC-20 Series)

column: YMC-Triart C8(YMC) 3.0 mmφ×150 mm column temperature: constant temperature near 40° C.

mobile phase: (SOLUTION A) 100 mM phosphate buffer (pH 5.5)/acetonitrile mixed solution (60:40), (SOLUTION B) water/acetonitrile mixed solution (1:4) gradient elution condition:

TABLE 9

| time (min) | mobile phase (SOLUTION A) (%) | mobile phase (SOLUTION B) (%) |
|---|---|---|
| 0-20 | 100 | 0 |
| 20-41 | 100→0 | 0→100 |
| 41-51 | 0 | 100 |
| 51-54 | 0→100 | 100→0 |
| 54-65 | 100 | 0 |

flow rate: 1.3 mL/min detector: ultraviolet absorption spectrophotometer (measurement wavelength: 214 nm)

TABLE 10

| mixing ratio | BAK-$C_{12}$ (%) | BAK-$C_{14}$ (%) | BAK-$C_{16}$ (%) |
|---|---|---|---|
| Sanisol C (manufactured by Koa Corporation) | 61.37 | 32.57 | 6.07 |
| Osvan S (manufactured by NIHON PHARMACEUTICAL CO., LTD.) | 85.0 | 15.0 | — |
| Benzalkonium Chloride Solution 50% Ph. Eur. (manufactured by FeF Chemicals A/S) | 68.3 | 31.7 | — |

TABLE 11

| | Example 36 | Example 37 | Example 38 | Example 39 | Example 40 | Example 41 | Example 42 |
|---|---|---|---|---|---|---|---|
| Compound A | 0.0005 | 0.001 | 0.001 | 0.001 | 0.001 | 0.001 | 0.001 |
| sodium dihydrogen phosphate | 0.1 | 0.1 | 0.1 | 0.1 | 0.1 | 0.1 | 0.1 |
| BAK mixture | 0.005* | 0.005* | 0.005* | 0.005* | 0.005* | 0.005* | 0.005* |
| tyloxapol | — | 0.001 | 0.005 | 0.01 | 0.02 | 0.05 | 0.1 |
| sodium hydroxide | q.s. | q.s. | q.s. | q.s. | q.s. | q.s. | q.s. |
| purified water | q.s. | q.s. | q.s. | q.s. | q.s. | q.s. | q.s. |
| pH | 7.5 | 7.5 | 7.5 | 7.5 | 7.5 | 7.5 | 7.5 |
| appearance (visual observation) | colorless clear | colorless clear | colorless clear | colorless clear | colorless clear | colorless clear | colorless clear |
| transmittance (600 nm) | 98.2% | 99.5% | 99.7% | 100.0% | 100.0% | 100.0% | 100.0% |

(unit of numerical values in Table: w/v %; q.s.: appropriate amount)
*BAK manufactured by NIHON PHARAMACEUTICAL Co., LTD.

TABLE 12

| | Example 43 | Example 44 | Example 45 | Example 46 | Example 47 | Example 48 |
|---|---|---|---|---|---|---|
| Compound A | 0.001 | 0.001 | 0.001 | 0.005 | 0.005 | 0.005 |
| sodium dihydrogen phosphate | 0.1 | 0.1 | 0.1 | — | — | — |
| boric acid | — | — | — | 0.1 | 0.1 | 0.1 |
| BAK mixture | 0.003* | 0.003** | 0.003*** | 0.003* | 0.003** | 0.003*** |
| tyloxapol | 0.05 | 0.05 | 0.05 | 0.05 | 0.05 | 0.05 |
| sodium hydroxide | q.s. | q.s. | q.s. | q.s. | q.s. | q.s. |
| purified water | q.s. | q.s. | q.s. | q.s. | q.s. | q.s. |
| pH | 7.5 | 7.5 | 7.5 | 8.5 | 8.5 | 8.5 |
| appearance (visual observation) | colorless clear | colorless clear | colorless clear | colorless clear | colorless clear | colorless clear |
| transmittance (600 nm) | 100.0% | 99.9% | 99.9% | 100.0% | 99.4% | 100.0% |

(unit of numerical values in Table: w/v %; q.s.: appropriate amount)

*BAK manufactured by NIHON PHARMACEUTICAL CO., LTD.;

**BAK manufactured by Kao Corporation;

***BAK manufactured by FeF Chemicals A/S (Experiment Results)

Similar results were obtained even when a commercially available product having a mixing ratio different from that of BAK-$C_{12}$/$C_{14}$ as BAK (Table 11, Example 36) was used. In addition, it was found that the clarity can be maintained, regardless of the kind of the BAK mixture, by adding tyloxapol even when the concentration of compound A was increased (Tables 11 and 12).

Formulation Example

According to the formulations shown in Table 13-1 to Table 13-2, compound A-containing ophthalmic solutions were prepared according to a conventional method (Formulation Examples 1-14).

TABLE 13-1

| component•content (w/v %) | Formulation Example 1 | Formulation Example 2 | Formulation Example 3 | Formulation Example 4 | Formulation Example 5 | Formulation Example 6 | Formulation Example 7 | Formulation Example 8 |
|---|---|---|---|---|---|---|---|---|
| Compound A | 0.0001 | 0.0003 | 0.0005 | 0.001 | 0.005 | 0.05 | 0.001 | 0.001 |
| sodium dihydrogen phosphate | 0.1 | 0.1 | 0.1 | 0.1 | 0.1 | 0.1 | — | — |
| boric acid | — | — | — | — | — | — | 0.1 | 0.1 |
| borax | — | — | — | — | — | — | q.s. | q.s. |
| tyloxapol | — | 0.001 | — | 0.001 | 0.001 | 0.2 | — | — |
| polysorbate 80 | — | — | — | — | — | — | 0.5 | — |
| polyoxyethylene hydrogenated castor oil 60 | — | — | — | — | — | — | — | 0.5 |
| sodium hydroxide | q.s. | q.s. | q.s. | q.s. | q.s. | q.s. | q.s. | q.s. |
| benzalkonium chloride | 0.005* | 0.005* | 0.005* | 0.005* | 0.005* | 0.005* | 0.005* | 0.005* |
| purified water | q.s. | q.s. | q.s. | q.s. | q.s. | q.s. | q.s. | q.s. |
| total amount (mL) | 100 | 100 | 100 | 100 | 100 | 100 | 100 | 100 |
| pH | 7.5 | 7.5 | 7.5 | 7.5 | 7.5 | 7.5 | 7.5 | 7.5 |

*BAK manufactured by NIHON PHARMACEUTICAL CO., LTD.

TABLE 13-2

| component•content (w/v %) | Formulation Example 9 | Formulation Example 10 | Formulation Example 11 | Formulation Example 12 | Formulation Example 13 | Formulation Example 14 |
|---|---|---|---|---|---|---|
| Compound A | 0.001 | 0.001 | 0.001 | 0.005 | 0.005 | 0.005 |
| sodium dihydrogen phosphate | 0.1 | 0.1 | 0.1 | — | — | — |
| boric acid | — | — | — | 0.1 | 0.1 | 0.1 |
| borax | — | — | — | q.s. | q.s. | q.s. |
| tyloxapol | 0.05 | 0.05 | 0.05 | 0.05 | 0.05 | 0.05 |
| sodium hydroxide | q.s. | q.s. | q.s. | q.s. | q.s. | q.s. |
| benzalkonium chloride | 0.003* | 0.003** | 0.003*** | 0.003* | 0.003** | 0.003*** |
| purified water | q.s. | q.s. | q.s. | q.s. | q.s. | q.s. |
| total amount (mL) | 100 | 100 | 100 | 100 | 100 | 100 |
| pH | 7.5 | 7.5 | 7.5 | 8.5 | 8.5 | 8.5 |

*BAK manufactured by NIHON PHARMACEUTICAL CO., LTD.;
**BAK manufactured by Kao Corporation;
***BAK manufactured by FeF Chemicals A/S

INDUSTRIAL APPLICABILITY

According to the present invention, an aqueous liquid preparation containing compound A having a PPAR δ agonist action and useful for the treatment of diseases such as meibomian gland dysfunction, corneal epithelial disorder, dry eye and the like, which is a clear aqueous liquid preparation capable of preventing white turbidity resulting from an interaction between compound A and benzalkonium chloride and superior in preservation stability can be provided by adding benzalkonium chloride in a particular concentration range.

The invention claimed is:

1. An aqueous liquid preparation comprising: (1) (3-{2-[4-isopropyl-2-(4-trifluoromethyl)phenyl-5-thiazolyl]ethyl}-5-methyl-1,2-benzisoxazol-6-yl)oxyacetic acid or a pharmaceutically acceptable salt thereof, and (2) at least one benzalkonium chloride, wherein benzalkonium chloride is represented by the formula:

$$[C_6H_5CH_2N(CH_3)_2]Cl$$

wherein R is an alkyl group having 8-18 carbon atoms, wherein the transmittance of the aqueous liquid preparation at wavelength 600 nm is not less than 98%, wherein the (3-{2-[4-isopropyl-2-(4-trifluoromethyl)phenyl-5-thiazolyl]ethyl}-5-methyl-1,2-benzisoxazol-6-yl)oxyacetic acid or the pharmaceutically acceptable salt thereof has a concentration selected from the range of the lower limit concentration of about 0.0002 w/v % and the upper limit concentration of about 0.05 w/v % relative to the total amount of the aqueous liquid preparation, wherein the benzalkonium chloride has a concentration of less than 0.05 w/v % or higher than 0.1 w/v % relative to the total amount of the aqueous liquid preparation when R is an alkyl group having 8 carbon atoms, wherein the benzalkonium chloride has a concentration of less than 0.05 w/v % or higher than 0.1 w/v % when R is an alkyl group having 10 carbon atoms, wherein the benzalkonium chloride has a concentration of less than 0.003 w/v % or higher than 0.01 w/v % relative to the total amount of the aqueous liquid preparation when R is an alkyl group having 12 carbon atoms, wherein the benzalkonium chloride has a concentration of less than 0.001 w/v % or higher than 0.002 w/v % relative to the total amount of the aqueous liquid preparation when R is an alkyl group having 14 carbon atoms, wherein the benzalkonium chloride has a concentration other than 0.001 w/v % relative to the total amount of the aqueous liquid preparation when R is an alkyl group having 16 carbon atoms, and wherein a mixture of the benzalkonium chlorides has a total concentration of less than 0.001 w/v % or higher than 0.002 w/v % relative to the total amount of the aqueous liquid preparation when the mixture comprises (i) a first benzalkonium chloride wherein R is an alkyl group having 12 carbon atoms and (ii) a second benzalkonium chloride wherein R is an alkyl group having 14 carbon atoms.

2. The aqueous liquid preparation according to claim 1, wherein R is an alkyl group having 8 carbon atoms, and the benzalkonium chloride has a concentration of less than 0.05 w/v % or higher than 0.1 w/v % relative to the total amount of the aqueous liquid preparation.

3. The aqueous liquid preparation according to claim 1, wherein R is an alkyl group having 10 carbon atoms, and the benzalkonium chloride has a concentration of less than 0.05 w/v % or higher than 0.1 w/v % relative to the total amount of the aqueous liquid preparation.

4. The aqueous liquid preparation according to claim 1, wherein R is an alkyl group having 12 carbon atoms, and the benzalkonium chloride has a concentration of less than 0.003 w/v % or higher than 0.01 w/v % relative to the total amount of the aqueous liquid preparation.

5. The aqueous liquid preparation according to claim 1, wherein R is an alkyl group having 14 carbon atoms, and the benzalkonium chloride has a concentration of less than 0.001 w/v % or higher than 0.002 w/v % relative to the total amount of the aqueous liquid preparation.

6. The aqueous liquid preparation according to claim 1, wherein R is an alkyl group having 16 carbon atoms, and the benzalkonium chloride has a concentration other than 0.001 w/v % relative to the total amount of the aqueous liquid preparation.

7. The aqueous liquid preparation according to claim 1, wherein R is an alkyl group having 18 carbon atoms.

8. The aqueous liquid preparation according to claim 1, comprising a mixture of (i) a first benzalkonium chloride wherein R is an alkyl group having 12 carbon atoms and (ii) a second benzalkonium chloride wherein R is an alkyl group having 14 carbon atoms, and the total concentration of the benzalkonium chloride mixture relative to the total amount of the aqueous liquid preparation is less than 0.001 w/v % or higher than 0.002 w/v %.

9. The aqueous liquid preparation according to claim 1, further comprising a surfactant.

10. The aqueous liquid preparation according to claim 9, wherein the surfactant is tyloxapol.

11. An ophthalmic solution comprising: (1) (3-{2-[4-isopropyl-2-(4-trifluoromethyl)phenyl-5-thiazolyl]ethyl}-5-methyl-1,2-benzisoxazol-6-yl)oxyacetic acid or a pharmaceutically acceptable salt thereof, and (2) at least one benzalkonium chloride, wherein benzalkonium chloride is represented by the formula:

$$[C_6H_5CH_2N(CH_3)_2R]Cl$$

wherein R is an alkyl group having 8-18 carbon atoms, wherein the transmittance of the aqueous liquid preparation at wavelength 600 nm is not less than 98%, wherein the (3-{2-[4-isopropyl-2-(4-trifluoromethyl)phenyl-5-thiazolyl]ethyl}-5-methyl-1,2-benzisoxazol-6-yl)oxyacetic acid or the pharmaceutically acceptable salt thereof has a concentration selected from the range of the lower limit concentration of about 0.0002 w/v % and the upper limit concentration of about 0.05 w/v % relative to the total amount of the aqueous liquid preparation, wherein the benzalkonium chloride has a concentration of less than 0.05 w/v % or higher than 0.1 w/v % relative to the total amount of the aqueous liquid preparation when R is an alkyl group having 8 carbon atoms, wherein the benzalkonium chloride has a concentration of less than 0.05 w/v % or higher than 0.1 w/v % when R is an alkyl group having 10 carbon atoms, wherein the benzalkonium chloride has a concentration of less than 0.003 w/v % or higher than 0.01 w/v % relative to the total amount of the aqueous liquid preparation when R is an alkyl group having 12 carbon atoms, wherein the benzalkonium chloride has a concentration of less than 0.001 w/v % or higher than 0.002 w/v % relative to the total amount of the aqueous liquid preparation when R is an alkyl group having 14 carbon atoms, and wherein the benzalkonium chloride has a concentration other than 0.001 w/v % relative to the total amount of the aqueous liquid preparation when R is an alkyl group having 16 carbon atoms, and wherein a mixture of the benzalkonium chlorides has a total concentration of less than 0.001 w/v % or higher than 0.002 w/v % relative to the total amount of the aqueous liquid preparation when the mixture comprises (i) a first benzalkonium chloride wherein R is an alkyl group having 12 carbon atoms and (ii) a second benzalkonium chloride wherein R is an alkyl group having 14 carbon atoms.

12. A method of preparing the aqueous liquid preparation of claim 1 comprising:

adding at least one benzalkonium chloride, wherein benzalkonium chloride is represented by the formula:

$$[C_6H_5CH_2N(CH_3)_2R]Cl$$

wherein R is an alkyl group having 8-18 carbon atoms to an aqueous liquid solution comprising (3-{2-[4-isopropyl-2-(4-trifluoromethyl)phenyl-5-thiazolyl]ethyl}-5-methyl-1,2-benzisoxazol-6-yl)oxyacetic acid or a pharmaceutically acceptable salt thereof, wherein the (3-{2-[4-isopropyl-2-(4-trifluoromethyl)phenyl-5-thiazolyl]ethyl}-5-methyl-1,2-benzisoxazol-6-yl)oxyacetic acid or the pharmaceutically acceptable salt thereof has a concentration selected from the range of the lower limit concentration of about 0.0002 w/v % and the upper limit concentration of about 0.05 w/v % relative to the total amount of the aqueous liquid preparation, wherein the benzalkonium chloride has a concentration of less than 0.05 w/v % or higher than 0.1 w/v % relative to the total amount of the aqueous liquid preparation when R is an alkyl group having 8 carbon atoms, wherein the benzalkonium chloride has a concentration of less than 0.05 w/v % or higher than 0.1 w/v % when R is an alkyl group having 10 carbon atoms, wherein the benzalkonium chloride has a concentration of less than 0.003 w/v % or higher than 0.01 w/v % relative to the total amount of the aqueous liquid preparation when R is an alkyl group having 12 carbon atoms, wherein the benzalkonium chloride has a concentration of less than 0.001 w/v % or higher than 0.002 w/v % relative to the total amount of the aqueous liquid preparation when R is an alkyl group having 14 carbon atoms, wherein the benzalkonium chloride has a concentration other than 0.001 w/v % relative to the total amount of the aqueous liquid preparation when R is an alkyl group having 16 carbon atoms, and wherein a mixture of the benzalkonium chlorides has a total concentration of less than 0.001 w/v % or higher than 0.002 w/v % relative to the total amount of the aqueous liquid preparation when the mixture comprises (i) a first benzalkonium chloride wherein R is an alkyl group having 12 carbon atoms and (ii) a second benzalkonium chloride wherein R is an alkyl group having 14 carbon atoms, and wherein the transmittance of the aqueous liquid preparation at wavelength 600 nm is not less than 98%.

13. The method according to claim 12, wherein R is an alkyl group having 8 carbon atoms, and wherein the benzalkonium chloride is added at a concentration of less than 0.05 w/v % or higher than 0.1 w/v % relative to the total amount of the aqueous liquid preparation.

14. The method according to claim 12, wherein R is an alkyl group having 10 carbon atoms, and wherein the benzalkonium chloride is added at a concentration of less than 0.05 w/v % or higher than 0.1 w/v % relative to the total amount of the aqueous liquid preparation.

15. The method according to claim 12, wherein R is an alkyl group having 12 carbon atoms, and wherein the benzalkonium chloride is added at a concentration of less than 0.003 w/v % or higher than 0.01 w/v % relative to the total amount of the aqueous liquid preparation.

16. The method according to claim 12, wherein R is an alkyl group having 14 carbon atoms, and wherein the benzalkonium chloride is added at a concentration of less than 0.001 w/v % or higher than 0.002 w/v % relative to the total amount of the aqueous liquid preparation.

17. The method according to claim 12, wherein R is an alkyl group having 16 carbon atoms, and wherein the benzalkonium chloride is added at a concentration other than 0.001 w/v % relative to the total amount of the aqueous liquid preparation.

18. The method according to claim 12, wherein R is an alkyl group having 18 carbon atoms.

19. The method according to claim 12, comprising adding a mixture of benzalkonium chlorides, wherein the mixture comprises (i) a first benzalkonium chloride wherein R is an alkyl group having 12 carbon atoms and (ii) a second benzalkonium chloride wherein R is an alkyl group having 14 carbon atoms, and the total concentration of the benzalkonium chloride mixture is less than 0.001 w/v % or higher than 0.002 w/v % relative to the total amount of the aqueous liquid preparation.

20. The ophthalmic solution according to claim 11, wherein R is an alkyl group having 8 carbon atoms, and the benzalkonium chloride has a concentration of less than 0.05 w/v % or higher than 0.1 w/v % relative to the total amount of the aqueous liquid preparation.

21. The ophthalmic solution according to claim 11, wherein R is an alkyl group having 10 carbon atoms, and the benzalkonium chloride has a concentration of less than 0.05 w/v % or higher than 0.1 w/v % relative to the total amount of the aqueous liquid preparation.

22. The ophthalmic solution according to claim 11, wherein R is an alkyl group having 12 carbon atoms, and the benzalkonium chloride has a concentration of less than 0.003 w/v % or higher than 0.01 w/v % relative to the total amount of the aqueous liquid preparation.

23. The ophthalmic solution according to claim 11, wherein R is an alkyl group having 14 carbon atoms, and the benzalkonium chloride has a concentration of less than 0.001 w/v % or higher than 0.002 w/v % relative to the total amount of the aqueous liquid preparation.

24. The ophthalmic solution according to claim 11, wherein R is an alkyl group having 16 carbon atoms, and the benzalkonium chloride has a concentration other than 0.001 w/v % relative to the total amount of the aqueous liquid preparation.

25. The ophthalmic solution according to claim 11, wherein R is an alkyl group having 18 carbon atoms.

26. The ophthalmic solution according to claim 11, comprising a mixture of (i) a first benzalkonium chloride wherein R is an alkyl group having 12 carbon atoms and (ii) a second benzalkonium chloride wherein R is an alkyl group having 14 carbon atoms, and the total concentration of the benzalkonium chloride mixture relative to the total amount of the aqueous liquid preparation is less than 0.001 w/v % or higher than 0.002 w/v %.

27. The ophthalmic solution according to claim 11, further comprising a surfactant.

28. The ophthalmic solution according to claim 27, wherein the surfactant is tyloxapol.

* * * * *

UNITED STATES PATENT AND TRADEMARK OFFICE
CERTIFICATE OF CORRECTION

PATENT NO. : 9,968,679 B2
APPLICATION NO. : 14/763304
DATED : May 15, 2018
INVENTOR(S) : Shikamura et al.

It is certified that error appears in the above-identified patent and that said Letters Patent is hereby corrected as shown below:

In the Claims

Claim 1, Column 18, Line 9, "$[C_6H_5CH_2N(CH_3)_2]Cl$" should read -- $[C_6H_5CH_2N(CH_3)_2R]Cl$ --.

Signed and Sealed this
Tenth Day of July, 2018

Andrei Iancu
*Director of the United States Patent and Trademark Office*